United States Patent
Casas et al.

(10) Patent No.: US 10,589,011 B2
(45) Date of Patent: Mar. 17, 2020

(54) FIELD-ORIENTED CONTROL FOR CONTROL OF BLOOD PUMP MOTOR

(71) Applicant: HEARTWARE, INC., Miami Lakes, FL (US)

(72) Inventors: Fernando Casas, Miami Lakes, FL (US); Carlos Reyes, Davie, FL (US); Justin Wolman, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 281 days.

(21) Appl. No.: 15/710,323

(22) Filed: Sep. 20, 2017

(65) Prior Publication Data

US 2018/0085507 A1    Mar. 29, 2018

Related U.S. Application Data

(60) Provisional application No. 62/398,667, filed on Sep. 23, 2016.

(51) Int. Cl.
*A61M 1/10* (2006.01)
*A61M 1/12* (2006.01)

(52) U.S. Cl.
CPC .......... *A61M 1/1086* (2013.01); *A61M 1/101* (2013.01); *A61M 1/1036* (2014.02);
(Continued)

(58) Field of Classification Search
USPC .................................................. 318/16, 17
See application file for complete search history.

(56) References Cited

U.S. PATENT DOCUMENTS

| | | | | |
|---|---|---|---|---|
| 4,000,446 A | * | 12/1976 | Vandevier | H02H 3/0935 361/31 |
| 4,538,196 A | * | 8/1985 | Sun | H02H 7/263 361/64 |

(Continued)

FOREIGN PATENT DOCUMENTS

| | | |
|---|---|---|
| WO | 2012071065 A1 | 5/2012 |
| WO | 2013056131 A1 | 4/2013 |

(Continued)

OTHER PUBLICATIONS

Renesas Electronics, YMCRPRX52t: RX62T Motor Control Evaluation Kit Quick Start Guide, D011011_11_V0100.

(Continued)

*Primary Examiner* — Bentsu Ro
(74) *Attorney, Agent, or Firm* — Christopher & Weisberg, P.A.

(57) ABSTRACT

A ventricular assist device includes a pump configured to pump blood of a patient. A motor is configured to operate the pump. First, second, and third conductors are coupled to the motor and are configured to supply electric current from a power supply to the motor in first, second, and third phases, respectively. A controller is configured to operate the motor using a Field Oriented Control (FOC) method, and if one from the group consisting of first, second and third conductors becomes unable to supply electric current to the motor, the controller continues to operate the motor using the FOC method using the phases of the two conductors that are able to supply electric current to the motor.

17 Claims, 8 Drawing Sheets

(52) U.S. Cl.
CPC ............ *A61M 1/122* (2014.02); *A61M 1/127* (2013.01); *A61M 1/1008* (2014.02); *A61M 1/1053* (2013.01)

(56) References Cited

U.S. PATENT DOCUMENTS

| | | | |
|---|---|---|---|
| 6,234,772 B1 | 5/2001 | Wampler et al. | |
| 6,351,048 B1 | 2/2002 | Schob et al. | |
| 6,387,037 B1* | 5/2002 | Bolling | A61M 1/10 600/16 |
| 6,572,530 B1* | 6/2003 | Araki | A61M 1/1086 600/17 |
| 8,512,013 B2 | 8/2013 | LaRose et al. | |
| 9,339,598 B2 | 5/2016 | LaRose et al. | |
| 2003/0191357 A1* | 10/2003 | Frazier | A61M 1/101 600/16 |
| 2004/0152944 A1* | 8/2004 | Medvedev | A61M 1/101 600/17 |
| 2010/0152526 A1* | 6/2010 | Pacella | A61M 1/102 600/17 |
| 2012/0245681 A1 | 9/2012 | Casas et al. | |
| 2014/0100413 A1 | 4/2014 | Casas et al. | |
| 2014/0357937 A1 | 12/2014 | Reyes et al. | |
| 2015/0109139 A1* | 4/2015 | Shanks | H04B 3/54 340/854.9 |
| 2016/0166211 A1 | 6/2016 | Brown et al. | |
| 2017/0185054 A1 | 6/2017 | Rudser | |

FOREIGN PATENT DOCUMENTS

| | | |
|---|---|---|
| WO | 2014113533 A1 | 7/2014 |
| WO | 2016086137 A1 | 6/2016 |

OTHER PUBLICATIONS

Renesas Electronics, RX600 Motor Control Evaluation Kit, Ready-to-use Platform for Evaluating Sensorless Vector Control and Position Control.
Renesas Electronics, RX62T, Three Shunt Sensorless Vector Control of PMSM with Internal Programmable Gain Amplifier (PGA), R01AN0902EU0200, Rev. 2.00, Jan. 31, 2014, pp. 16.
Renesas Electronics, RX62T Motor Control Evaluation Kit, User Manual: Hardware, RX Family / RX600 Series / RX62T Group, Rev.1.00, Jan. 2012.
Texas Instruments, DRV830x-HC-C2-KIT Hardware Reference Guide, Version 1.0—Aug. 2011.
Bilal Akin and Manish Bhardwaj, Texas Instruments, Trapezoidal Control of BLDC Motors Using Hall Effect Sensors, Version 1.0—Feb. 2010.
Copely Controls Corp.—Article, What is 'Filed Oriented Control' and what good is it?
Texas Instruments, RM48L952 16- and 32 Bit RISC Flash Microcontroller, SPNS177B—Sep. 2011—Revised Jul. 2013.
International Search Report and Written Opinion dated Dec. 18, 2017 for corresponding International Application No. PCT/US2017052492; International Filing Date: Sep. 20, 2017 consisting of 12-pages.

* cited by examiner

FIELD-ORIENTED CONTROL FOR CONTROL OF BLOOD PUMP MOTOR

CROSS-REFERENCE TO RELATED APPLICATION

This application is related to and claims priority to U.S. Provisional Patent Application Ser. No. 62/398,667, filed Sep. 23, 2016, entitled FIELD-ORIENTED CONTROL FOR CONTROL OF BLOOD PUMP MOTOR, the entirety of which is incorporated herein by reference.

STATEMENT REGARDING FEDERALLY SPONSORED RESEARCH OR DEVELOPMENT n/a

TECHNICAL FIELD

The present invention relates to blood pumps powered by electric motors and more particularly to ventricular assist devices.

BACKGROUND

It is often necessary to provide an implanted pump to assist the heart of a human or a non-human animal subject with blood circulation, or as a substitute for the subject's heart. Examples of such implanted pumps include a ventricular assist device (VAD) implanted in a patient's body to take over some or all of the pumping function of the heart, as well as other cardiac assist devices and artificial heart pumps.

VADs having a brushless motor are known. In a known configuration, a VAD may include a housing and a stator having a plurality of motor windings disposed around the housing. The VAD also includes a rotor disposed within the housing. The rotor includes a magnet, typically a permanent magnet. The stator and rotor constitute a brushless motor. A rotating magnetic field is created and maintained by using an appropriate multi-phase sequence of excitations to supply the stator phases. The magnet in the rotor tends to align itself with the magnetic field, and thus the rotor spins about its axis and impels blood through the housing. Methods and controllers using variations of trapezoidal commutation for operating VADs are known. For instance, a 120° trapezoidal method using three phases involves exciting or driving each winding for 120° of the 360° electrical rotation cycle and leaving the winding un-driven for 60°.

SUMMARY

The present invention advantageously provides a ventricular assist device includes a pump configured to pump blood of a patient. A motor is configured to operate the pump. First, second, and third conductors are coupled to the motor and are configured to supply electric current from a power supply to the motor in first, second, and third phases, respectively. A controller is configured to operate the motor using a Field Oriented Control (FOC) method, and if one from the group consisting of first, second and third conductors becomes unable to supply electric current to the motor, the controller continues to operate the motor using the FOC method using the phases of the two conductors that are able to supply electric current to the motor.

In another aspect of this embodiment, the controller is configured to calculate voltage and current vectors, and wherein the controller is configured to commutate the motor based upon the calculated voltage and current vectors.

In another aspect of this embodiment, the device further includes first, second, and third shunts connected to the first, second and third conductors, respectively, wherein the controller is configured to calculate the current vectors using the first, second, and third shunts.

In another aspect of this embodiment, when one from the group consisting of the first, second, and third conductors is unable to supply current to the motor, the controller is configured to start operation of the motor using the two phases of the conductors that are able to supply current to the motor.

In another aspect of this embodiment, the controller is configured to output signals representative of vector control variables including a torque and a slip angle of the motor.

In another aspect of this embodiment, the pump includes a housing configured for implantation within the body of the patient, the housing having a blood inlet for connection to a ventricle of the patient and a blood outlet for connection to an artery of the patient, wherein the motor is disposed within the housing.

In another aspect of this embodiment, the controller is disposed in a casing remote from the motor, and wherein the controller is electrically connected to the motor.

In another aspect of this embodiment, the motor is a brushless DC motor, and wherein the power supply connected to the motor is a DC power supply.

In another embodiment, a method for operating a ventricular assist device, the ventricular device including a pump, a motor connected to the pump, a controller connected to the motor, and a power source supplying power to the motor through first, second, and third phase connections includes operating three-phase excitation of the motor through the first, second, and third phase connections to drive the motor and pump using a Field Oriented Control (FOC) method. If one of the first, second, and third phase connections fails, continuing to drive the motor and pump using the FOC method using the two phase connections that have not failed.

In another aspect of this embodiment, the controller operates three-phase excitation of the motor based on motor current measurements of the first, second, and third phases provided to the controller from first, second and third shunts, respectively.

In another aspect of this embodiment, continuing to drive the motor includes starting the motor using the two phase connections that have not failed.

In yet another embodiment, a method for operating a blood pump implanted in a patient, the blood pump including a rotor with permanent magnetic poles for rotation around an axis, and a plurality of stator windings in magnetic communication with the magnetic poles of the rotor includes supplying power to the blood pump using a Field Oriented Control (FOC) method. If one of the stator windings of the blood pump fails, continuing to supply power to the blood pump over the remaining stator windings using the FOC method.

In another aspect of this embodiment, the motor is a brushless DC motor, and wherein the method further includes calculating voltage and current vectors and commutating the brushless DC motor based upon calculated voltage and current vectors.

In another aspect of this embodiment, the current vectors are calculated using a plurality of shunts, each shunt connected to a corresponding stator winding.

In another aspect of this embodiment, the method further includes that if one of the stator windings of the blood pump fails during startup, starting to supply power to the blood pump over the remaining stator windings using the FOC method.

In another aspect of this embodiment, the method further includes determining vector control variables comprising a torque and a slip angle of the rotor; wherein the supply power to the blood pump is controlled by signals representative of the vector control variables.

In yet another embodiment, a control circuit for operating a blood pump implanted in a patient, the blood pump including a rotor with permanent magnetic poles for rotation around an axis, and a plurality of stator windings in magnetic communication with the magnetic poles of the rotor, the control circuit being configured to supply power to the blood pump using a Field Oriented Control (FOC) method and if one of the stator windings of the blood pump fails, continuing to supply power to the blood pump over the remaining stator windings using the FOC method.

In another aspect of this embodiment, the control circuit is further configured to, during startup of the blood pump, supply power to the blood pump over the remaining stator windings using the FOC method if one of the stator windings of the blood pump fails.

In another aspect of this embodiment, the control circuit is further configured to determine vector control variables comprising a torque and a slip angle of the rotor; and wherein the supply of power to the blood pump is controlled by signals representative of the vector control variables.

In another aspect of this embodiment, the control circuit is further configured to calculate voltage and current vectors and to commutate the motor based upon the calculated voltage and current vectors.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

Figure 1:
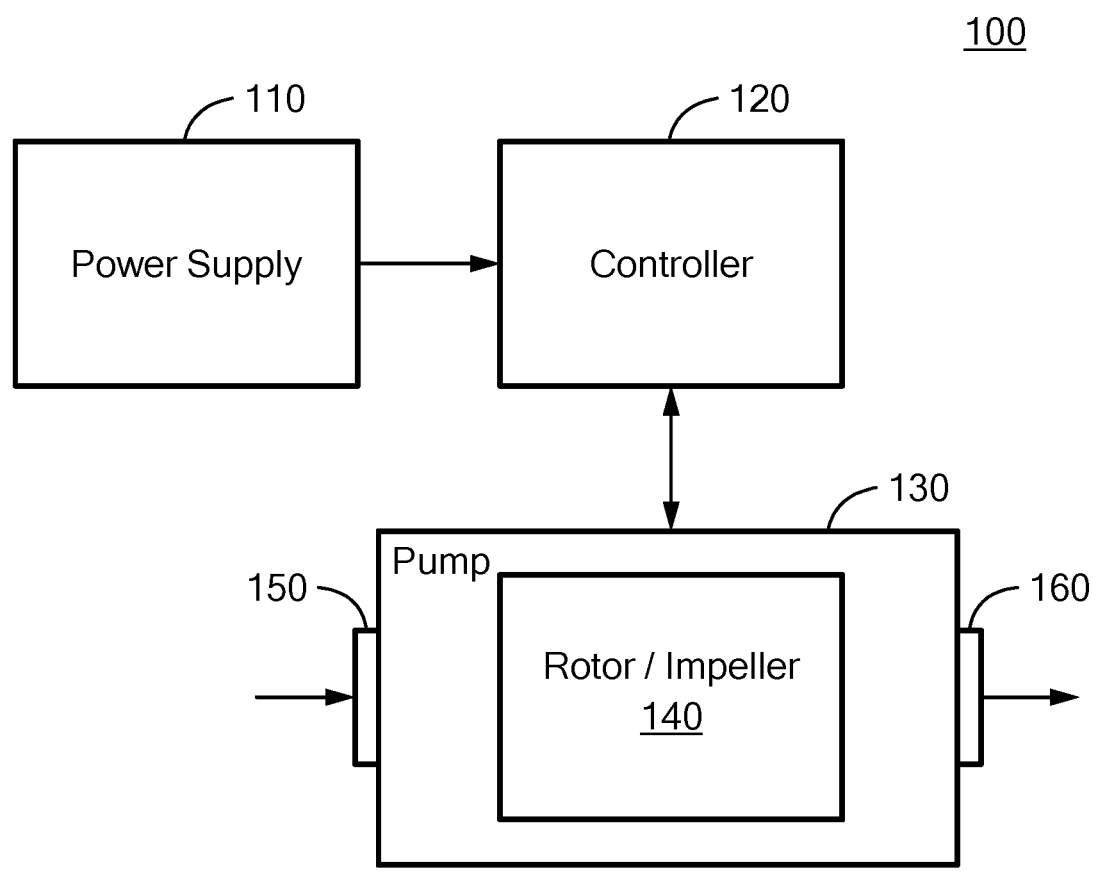
FIG. 1 is a schematic illustration of a pump system, according to an embodiment of the disclosure.

The following discussion describes, in detail, various aspects and embodiments of the present disclosure. This discussion should not be construed as limiting the disclosure to those particular aspects or embodiments. Rather, practitioners skilled in the art will recognize numerous other aspects and embodiments as well, which are within the scope of the present disclosure. Additionally, in describing the embodiments of the present disclosure illustrated in the drawings, specific terminology will be used for the sake of clarity. However, the disclosure is not intended to be limited to the specific terms so selected.

FIG. 1 is a schematic illustration of an example pump system 100 in accordance with an aspect of the disclosure. The system 100 includes a power supply 110, a controller 120, a pump 130 and a rotor 140. The pump 130 may include a housing (not shown), such that the rotor is disposed within the housing and rotates about an axis. The pump 130 is adapted to receive a fluid, for example blood, at an input end 150 of the housing and eject the fluid at the output end 160 of the housing.

Figure 2:
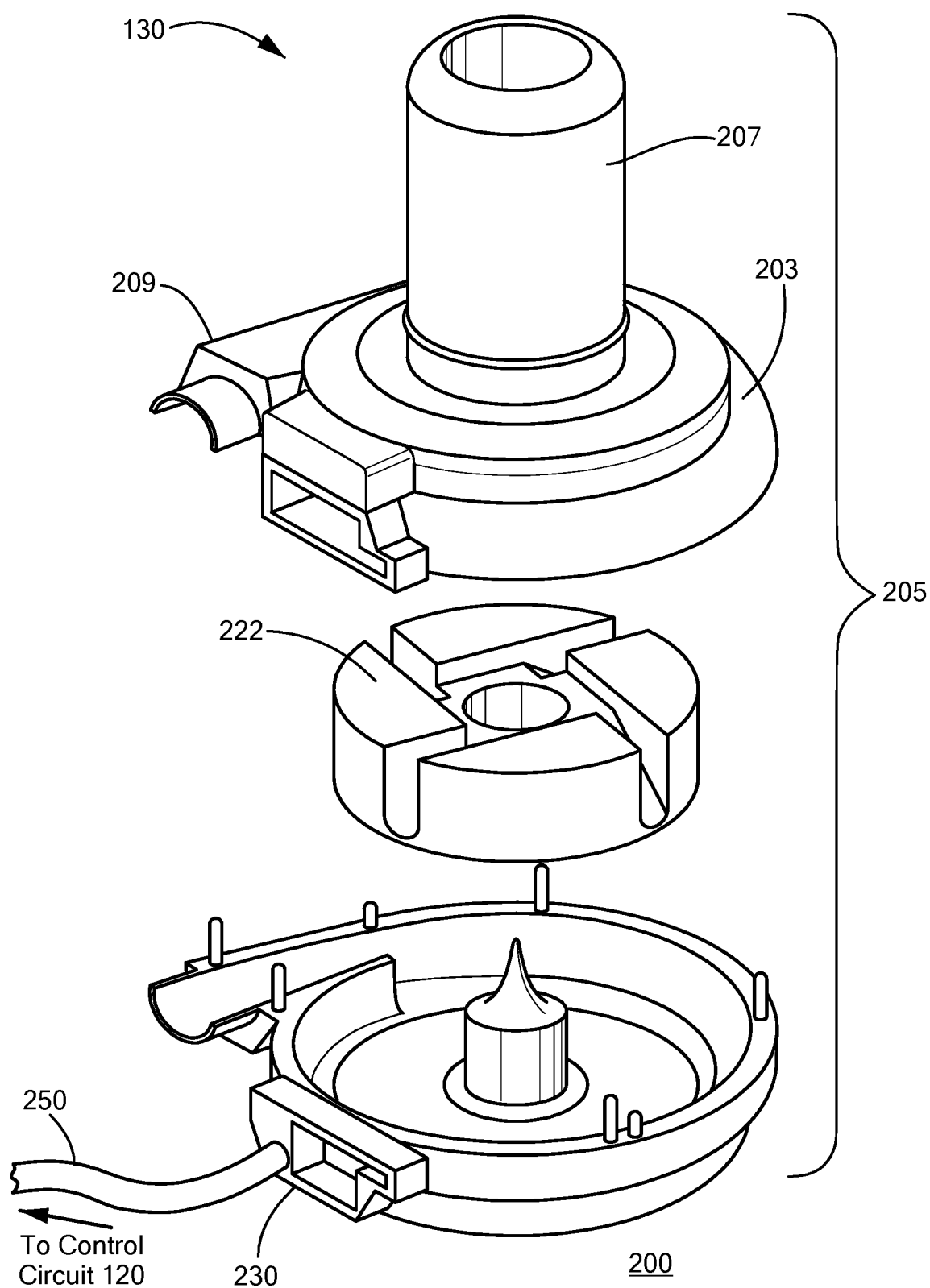
FIG. 2 illustrates an exploded view of an HVAD® pump.

In one example, the pump 130 may be a centrifugal pump, such as the HVAD® Pump manufactured by HeartWare Inc. in Miami Lakes, Fla., USA. The HVAD® Pump is further described in U.S. Pat. Nos. 6,234,772 and 8,512,013, the disclosures of which are incorporated by reference herein. As depicted in FIG. 2, the pump 130 includes a housing 205 consisting of interlocking casings to form a closed pumping chamber 203 between them. Blood is supplied to the pump 130 through an axial inlet cannula 207 adapted for apical insertion into a heart ventricle. The cannula 207 is affixed to or may be integral with the housing 205 and is in fluid flow communication with the pumping chamber 203. Blood exits the pumping chamber 203 through an outlet opposite the inlet cannula 207 in a direction substantially perpendicular to the longitudinal axis of the inlet cannula 207. A motor rotor or pump impeller 222 is located within the pumping chamber 203. In operation, blood entering the cannula 207 from a heart ventricle passes into the pumping chamber 203 where it is engaged by the rotating impeller 222. Blood entering the pumping chamber from the cannula 207 is redirected from axial flow exiting the cannula to a radial flow within which the impeller 222 is submerged. The housing 205 may contain an electrical feed through connector 230 for a power and control cable to supply power to the electrical motor of the pump. The cable feed 250 carrying a plurality of cables is connected to the pump through the connector 230. The cables in the feed 250 may carry electrical power, and control instructions between the controller 120 and the pump 130.

In another example, the pump 130 may be an axial flow pump, such as that used in the MVAD® ventricular assist device, also manufactured by HeartWare Inc. The MVAD® pump is further described in U.S. Pat. No. 9,339,598, the disclosure of which is incorporated by reference herein. As depicted in the example axial pump of FIGS. 3A and 3B, the pump 130 comprises a substantially cylindrical outer enclosure or cannula 302A. The cannula 302A may have the slightly rounded or bullet shaped front or inlet end of reduced diameter having inlet 316 through which blood enters the pumping chamber. The pumping chamber is defined by the substantially tubular interior housing 304 having an external diameter smaller than the internal diameter of the cannula. The cannula 302A and tubular housing 304 may be made of a biocompatible non-magnetic material such as titanium or ceramic. The motor stator ring 310 may be located on the outside of the housing 304 and within the cannula 302A in the annular space formed between the housing 304 and the cannula 302A. The three phase control conductors for the coils of the stator ring 310 are connected through the power and control cable conduit 320K that exits the pump through a port 318, which may be defined as part of a volute 306. A rotor 308, of the type described in detail above, may be magnetically or hydrodynamically suspended in operation within the housing 304 and centered within the stator ring 310 to provide an axial flow of the blood or fluid entering the inlet 316.

Figure 3A:
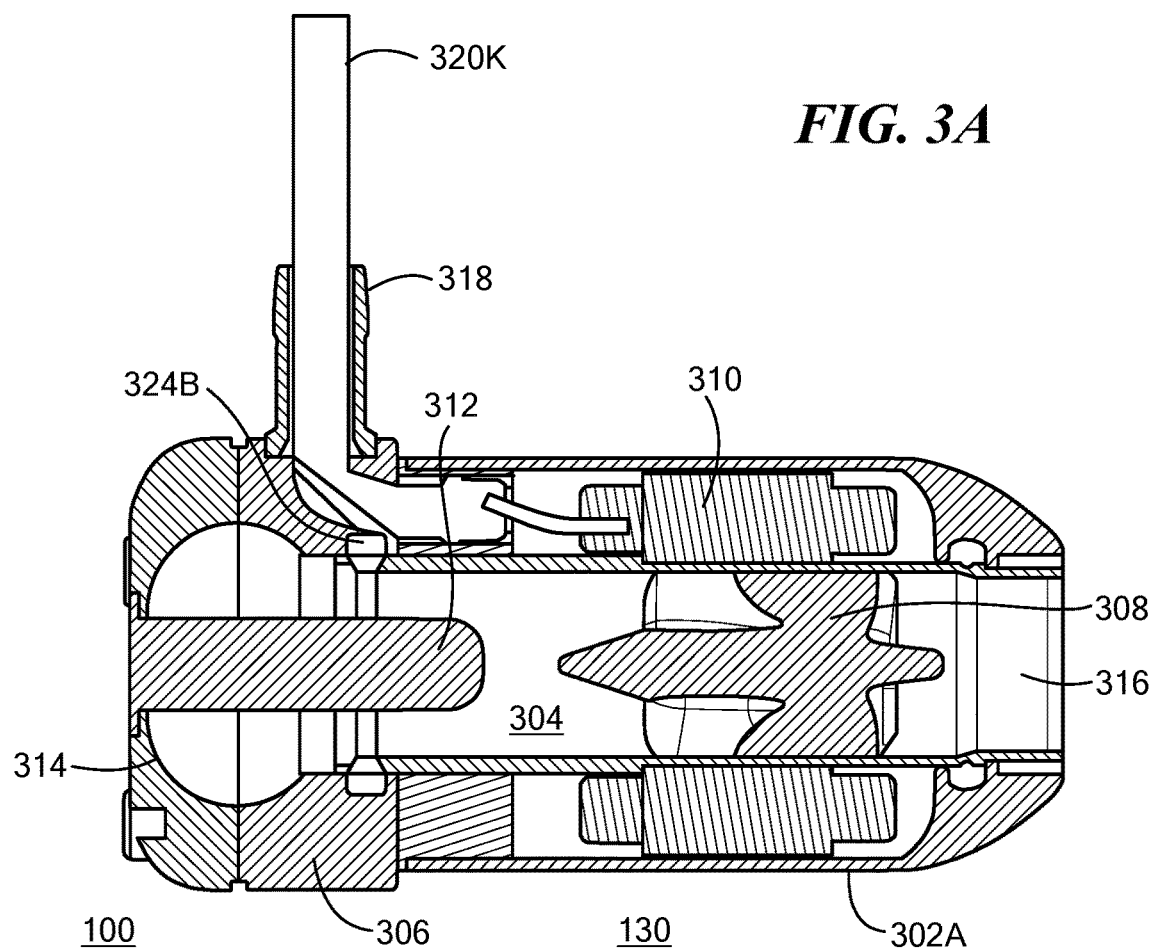
FIGS. 3A and 3B illustrate an exploded view of an MVAD® pump.
Figure 3B:
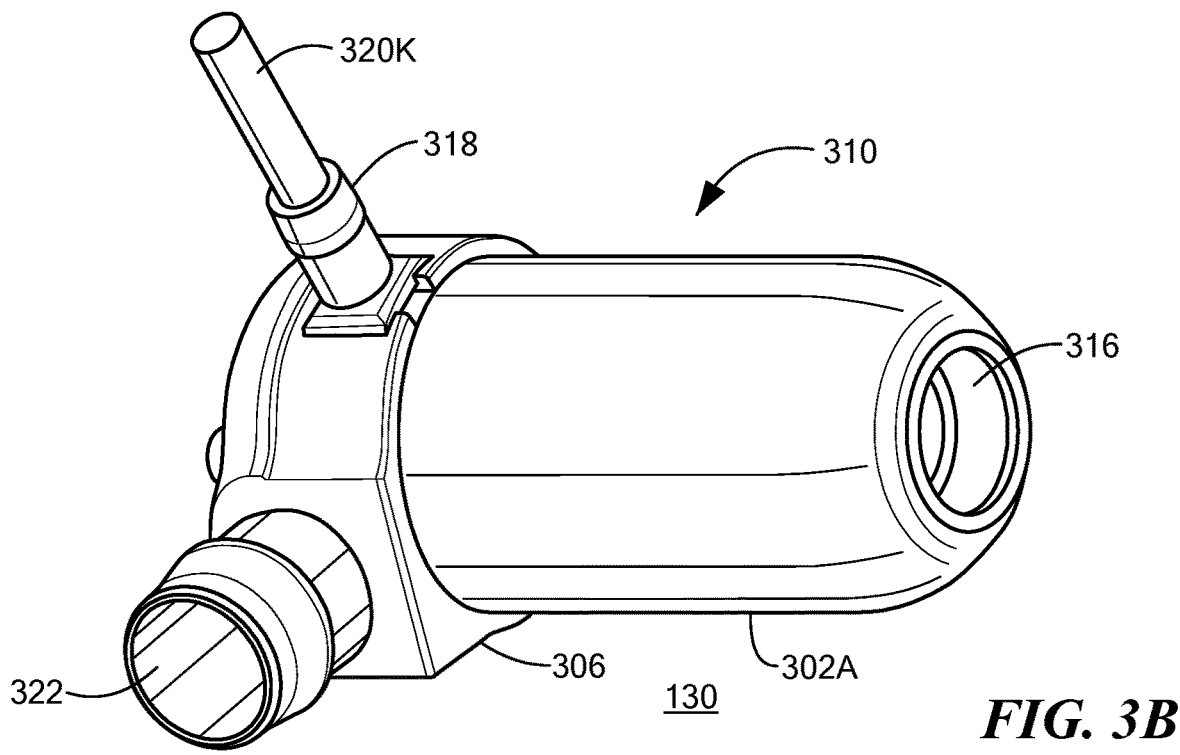

While the incorporation of a volute is not necessary with an axial flow pump, it is an optional embodiment for improving blood flow characteristics to further minimize thrombus formation and increase pressure of the pumped blood as it enters the vascular system. In the embodiment of FIGS. 3A and 3B, the pump includes a volute 306 sealed to the cannula 302a and the tubular housing 304 in a fluid-tight connection such that blood pumped by the rotor 308 is moved into a central chamber 314 of the volute 306. An O-ring 324B may be used to ensure a fluid-tight connection of the volute to the inner tubular housing 304. One or more screws (not shown) may be used to secure a hermetic connection. The volute chamber 314 may be annular in cross section as defined by a downstream center post 312 projecting inwardly along the pump axis from the base of the volute along the rotational axis of the pump rotor 308. The center post 312 extends toward but does not contact the downstream end of the rotor 308, and may be a dome-topped cylinder (as shown) or may be another shape that serves to affect the flow of blood discharged from the pump rotor. In other configurations, center post 312 is not included. Blood driven by the rotor 308 and entering the volute chamber from the pump chamber of the axial flow pump has a rotational or spiraling momentum around the rotational axis of the rotor. The rotational momentum of the flow creates lower pressure areas in a central portion of the blood flow just downstream of the rotor. To some extent the lower pressure area is alleviated by a tapered axial extension at the trailing edge of the rotor. The center post 312 also tends to fill this lower pressure area in the downstream rotational blood flow characteristics as the blood enters the chamber 314 of the volute. Blood thereafter fills the annular chamber 314 of the volute and the fluid pressure of the system causes the blood stream to flow in a substantially centrifugal direction through the chamber 314 to the volute discharge or outlet 322, thereby establishing the output pressure. In this embodiment, the volute is bladeless and the discharge blood flow is in accord with the longitudinal nature of the blood flow within the vascular system. The HVAD® and MVAD® pump designs discussed herein are intended merely as examples.

The pump may be arranged so that while the rotor is in motion, it is levitated within the housing by contactless bearings such as magnetic bearings, hydrodynamic bearings or a combination of the two. The pump may include a sensorless three-phase brushless direct-current (BLDC) motor with a stator having three windings controlled by a different respective phase U, V, W, of a power input for three-phase motor control. The BLDC motor includes an inverter circuit to convert a DC input to the three-phase output. Alternatively, the pump may receive an alternating current (AC) three-phase input. Examples of three-phase motor control methods and devices are provided in commonly owned U.S. Application No. 62/271,278, the disclosure of which is incorporated herein in its entirety.

The pump also connects to a power source (e.g., external AC power supply, external battery, implanted battery, or any combination thereof) to supply power to the motor. Electric current from the power source may be provided to each winding of the motor over a respective wire.

The pump is constructed and arranged so that it can be implanted within the body of a human or other mammalian subject. The inlet 150 of the pump is adapted for connection to a ventricle of the heart, whereas the outlet 160 is adapted for connection to an artery. For example, the inlet of the HVAD® pump typically is connected to the left ventricle of the subject by a flexible inflow cannula, and to the aorta by a flexible outflow cannula. The MVAD® pump may be mounted partially or entirely within the left ventricle, with the inlet of the pump communicating with the ventricle and with the outlet of the pump communicating with the aorta through an outflow cannula.

Figure 4:
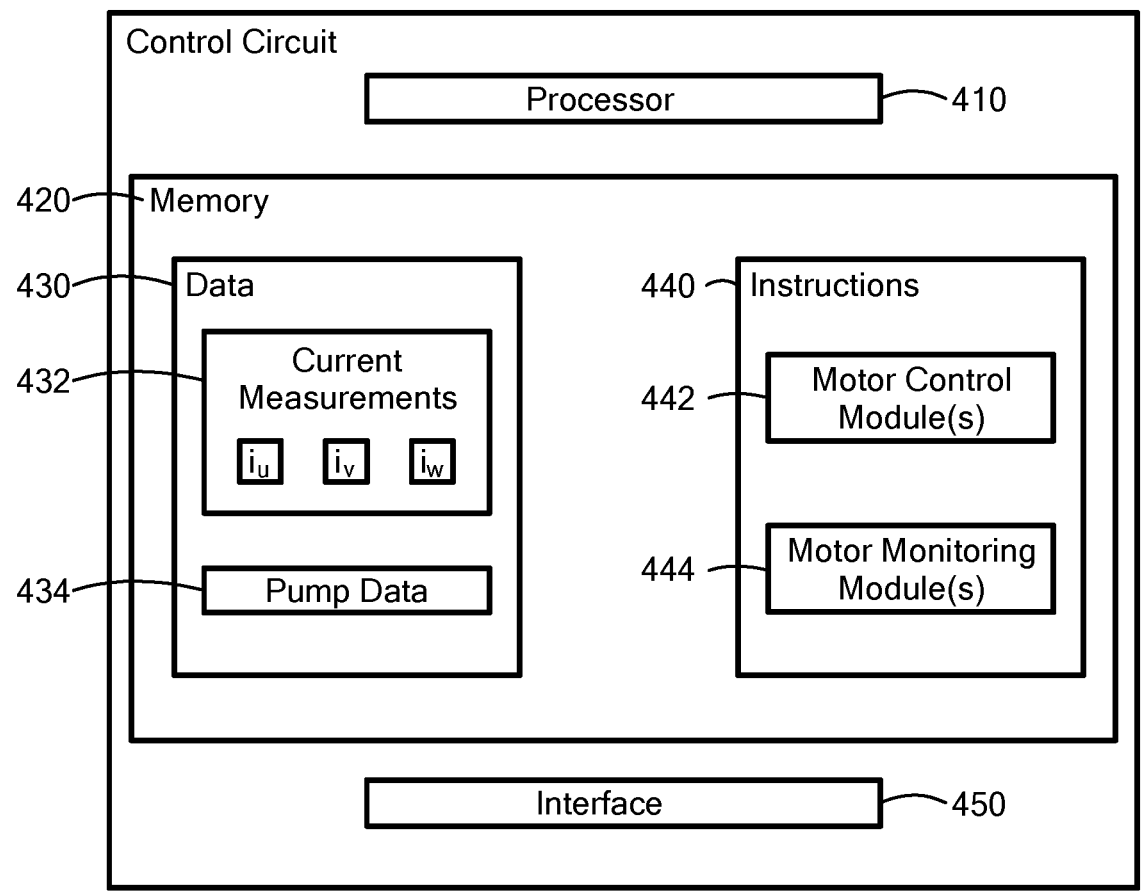
FIG. 4 is a block diagram of a control circuit, according to an embodiment of the disclosure.
Figure 4:
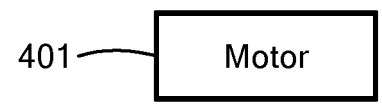

FIG. 4 shows an example control circuit 400 capable of monitoring and controlling startup and subsequent operation of a motor according to the routines of the present disclosure. The control circuit 400 may be coupled to the motor to control operation of the motor. Such coupling may be via one or more cables implanted within the patient. The control circuit 400 includes a processor 410, a memory 420 and an interface 450 for interfacing with the motor. Memory 420 stores information accessible by processor 410, including instructions 440 that may be executed by the processor 410. The memory 420 also includes data 430 that may be retrieved, manipulated or stored by the processor 410. The memory 420 may be of any type capable of storing information accessible by the processor 410, such as a hard-drive, memory card, ROM, RAM, DVD, CD-ROM, write-capable, and read only memories. The processor 410 may be any well-known processor, such as commercially available processors. Alternatively, the processor 410 may be a dedicated controller such as an ASIC.

Data 430 may be retrieved, stored or modified by processor 410 in accordance with the instructions 440. The data may also be formatted in any computer-readable format such as, but not limited to, binary values, ASCII or Unicode. Moreover, the data 430 may comprise any information sufficient to identify the relevant information, such as numbers, descriptive text, proprietary codes, pointers, references to data stored in other memories (including other network locations) or information that is used by a function to calculate the relevant data.

The control circuit 400 includes hardware and software for controlling the various aspects of the operation of the motor. The control circuit 400 is coupled to the motor 401 through the interface 450 to collect at least some of data 430 from the motor 401. For example, data 430 may include electrical current measurements 432 of the motor windings. The current measurements may be provided from current sensors, such as first, second and third shunts $R_1$, $R_2$, $R_3$ for measuring the respective currents $i_u$, $i_v$, $i_w$ of the motor windings. In one example, each of the shunts may be connected to a respective amplifier or programmable gain amplifier (PGA), to amplify the measured voltage across the shunt. Given the known resistance of each shunt, the amplified voltages may be converted back into current measurements. An analog to digital (A/D) converter may also be included for receiving the amplified voltages and converting them into corresponding digital signals to be received by the control circuit 400.

The data may optionally include pump data 434, such as flow rate of blood exiting the pump, flow pulsatility, differential pressure across the pump, motor speed, and current supplied to the motor, etc.

The instructions 440 stored in the memory 420 may include one or more instruction sets or modules, for performing certain operations in accordance with the present disclosure. One such module may be a motor control module 442 for controlling operation of the motor 401 (e.g., increasing or decreasing current supplied to the motor), such as in accordance with the FOC routines described herein. The instructions may also include one or more motor monitor modules 444 for monitoring operation of the motor. Examples of motor control and monitoring modules may be found in any of the commonly owned and copending U.S. application Ser. Nos. 13/355,297, 13/951,302, 14/294,448, 14/950,467, 62/266,871 and 62/271,618, the disclosures of which are incorporated herein by reference in their entireties.

Figure 5:
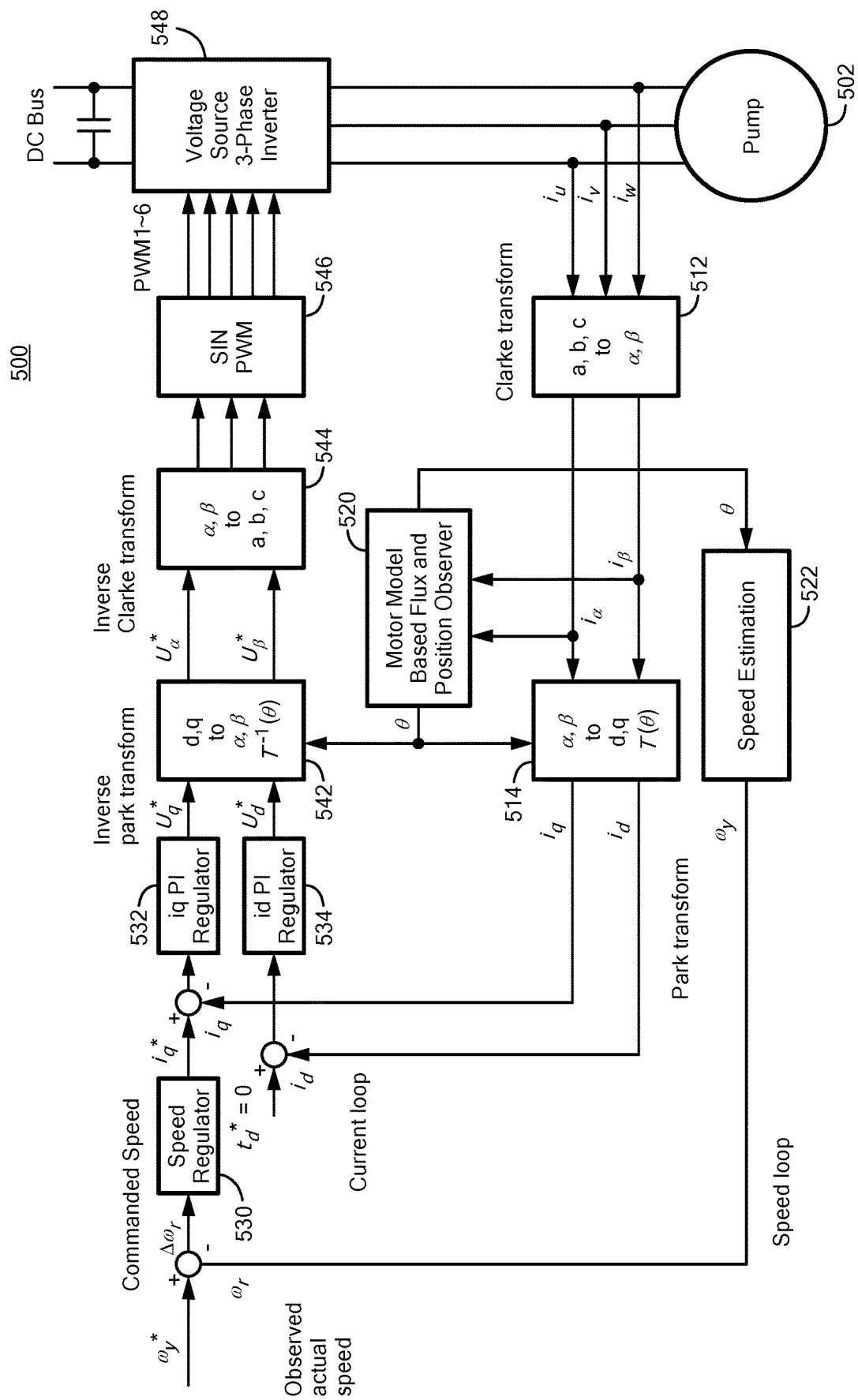
FIG. 5 is a block diagram illustrating three-shunt sensorless field-oriented control of a motor, according to an embodiment of the disclosure.

FIG. 5 is a block diagram 500 illustrating an implementation of a three-shunt sensorless field-oriented control (FOC) method for controlling a pump 502. In an exemplary embodiment, the pump has three stator windings and three alternating currents $i_u$, $i_v$, $i_w$ flowing therethrough, which are 120° apart in phase. The measured phase currents $i_u$, $i_v$, $i_w$ are first Clarke-transformed (512) to a static orthogonal [α, β] frame of reference, each of the α and β axes being 90° apart from one another. The Clarke-transform yields transformed currents $i_\alpha$ and $i_\beta$. The transformed currents $i_\alpha$, $i_\beta$ are then Park-transformed (514) to a rotor frame of reference [d, q], which is also an orthogonal frame, and is aligned with the magnetic field axes. The d (or direct) axis of the [d,q] frame of reference is aligned with the rotor flux, with the q (or quadrature) axis perpendicular thereto. The Park-transform yields transformed currents $i_d$ and $i_q$. Current $i_d$ is used to control the magnetic flux of the stator windings, and current $i_q$ is used to control the torque.

In the illustrated sensorless implementation, a motor model (520) is used to calculate the rotor angle θ based on currents $i_\alpha$ and $i_\beta$. The Park-transform uses the rotor angle θ to calculate currents $i_d$ and $i_q$. Rotor speed is also estimated (522) based on changes in the measured angle θ over time. Alternatively, in an FOC method that is not sensorless, a separate sensor may be used to measure the rotor angle and estimate the rotor speed.

The measured speed may be provided to a speed regulator in combination with a speed input in order to provide regulation of the rotor's speed (530). A control algorithm (532, 534) then uses a proportional-integral (PI) or proportional-integral-derivative (PID) controller to calculate each of the required voltages [$U_d$, $U_q$] for the torque and flux at the desired speed based on the transformed currents $i_d$ and $i_q$. These voltages [$U_d$, $U_q$] are then transformed back to the [u, v, w] frame of reference using an inverse Park transform (542) and an inverse Clarke transform (544), and a pulse-width modulation (PWM) duty cycle (546) is calculated based on the transformed voltages. The PWM is then provided to a 3 phase inverter (548) for regulating an amount of voltage from a DC voltage source (shown as DC Bus in FIG. 5) to be provided to the pump in accordance with the calculated duty cycle.

Figure 6:
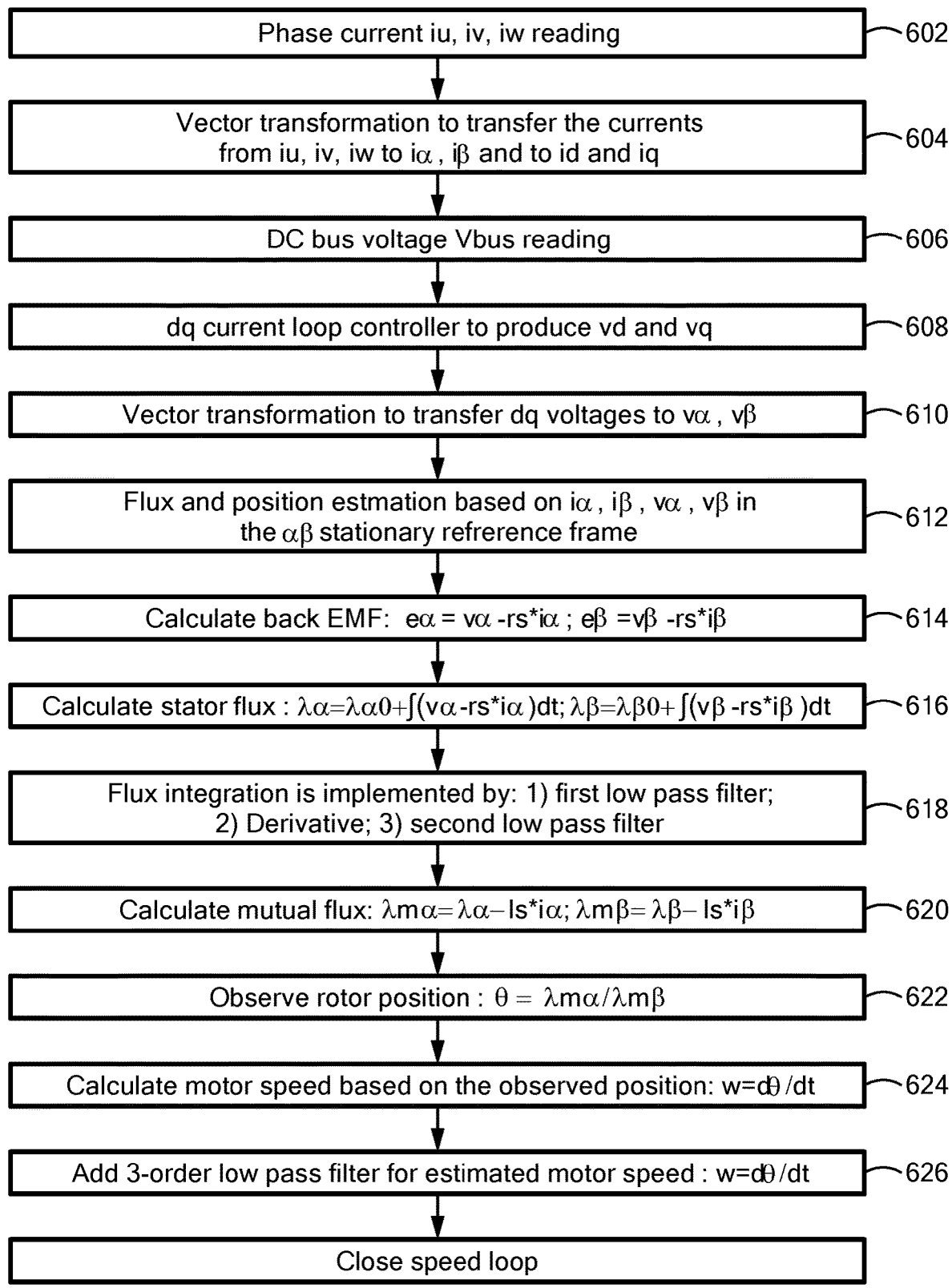
FIG. 6 is a flow diagram for a three-shunt sensorless field-oriented control algorithm for operating the VAD.

FIG. 6 illustrates a flow chart 600 for implementing a method of three shunt sensorless FOC in accordance with the present disclosure. At 602, phase currents $i_u$, $i_v$, $i_w$ are measured. At 604, a vector transformation is conducted, transferring the measured currents $i_u$, $i_v$, $i_w$ to $i_\alpha$, $i_\beta$ and then to $i_d$ and $i_q$. At 606, the DC bus voltage $V_{bus}$ is measured. The controller (e.g., PI, PID) then outputs signals representative of vector control variables comprising a torque and slip angle of the motor. At 608, the controller produces voltages $v_d$ and $v_q$ based on the currents $i_d$ and $i_q$ and $V_{bus}$. At 610, the vd and vq voltages are transferred to the [α, β] frame of reference. At 612, flux and position are estimated based on the measured currents and calculated voltages in the [α, β] frame of reference. At 614, a back electromotive force (BEMF) vector is calculated in the [α, β] frame of reference based on the difference between the calculated voltages and the measured voltages (which are the currents $i_\alpha$, $i_\beta$ multiplied by the resistance of the stator resistors). At 616, stator flux is calculated in the [α, β] frame of reference based on the integral of the BEMF. At 618, flux integration is performed by an integrator and use a low pass filter before and after. At 620, mutual flux is calculated based on the stator flux components. At 622, the rotor angle θ is estimated based on the mutual flux. At 624, the motor speed is estimated based on the rotor angle, as observed over time (e.g., two consecutive rotor angle computations). Lastly, at 626, the estimated motor speed is low-pass filtered to derive a determined motor speed. Using the above described method, the controller is capable of commutating the motor based on measured voltages/currents of the rotor stator windings.

One advantage of using an FOC method, as described above, is increased motor efficiency, which may lead to longer battery-run times for patients with an implanted VAD. Another advantage of the above described FOC methods is that precise control of the pump may allow for commutation of the motor to begin operation or to continue operation with only two phases. For example, if the motor is started using the three stator conductors, and then one of the conductors were to disconnect (e.g., due to connector contamination, partial driveline fractures, etc.), the FOC method could continue to be used to operate the pump. Where FOC is run on two conductors, the current of the third conductor would be measured as 0, and the transformed currents $i_\alpha$ and $i_\beta$ would be the converted vectors of the two non-zero currents in the phase-based [u, v, w] frame of reference. Still further, independent relationship between one or several FOC variables and the pump flow may be developed. A combination of BEMF and the FOC variables may provide a faster estimate of the pump flow during the pulsatile operation of the VAD, which may allow for fast suction detection and/or occlusion detection.

FIGS. 7-10 illustrate power consumption as a function of flow for both an MVAD® pump and an HVAD® pump. As can be seen from the figures, the pumps generally consume more power when operating using two conductors instead of three conductors. In some cases, operation using two conductors is still more power efficient than other speed control methods (e.g., PAL PQ for the MVAD®).

Figure 7:
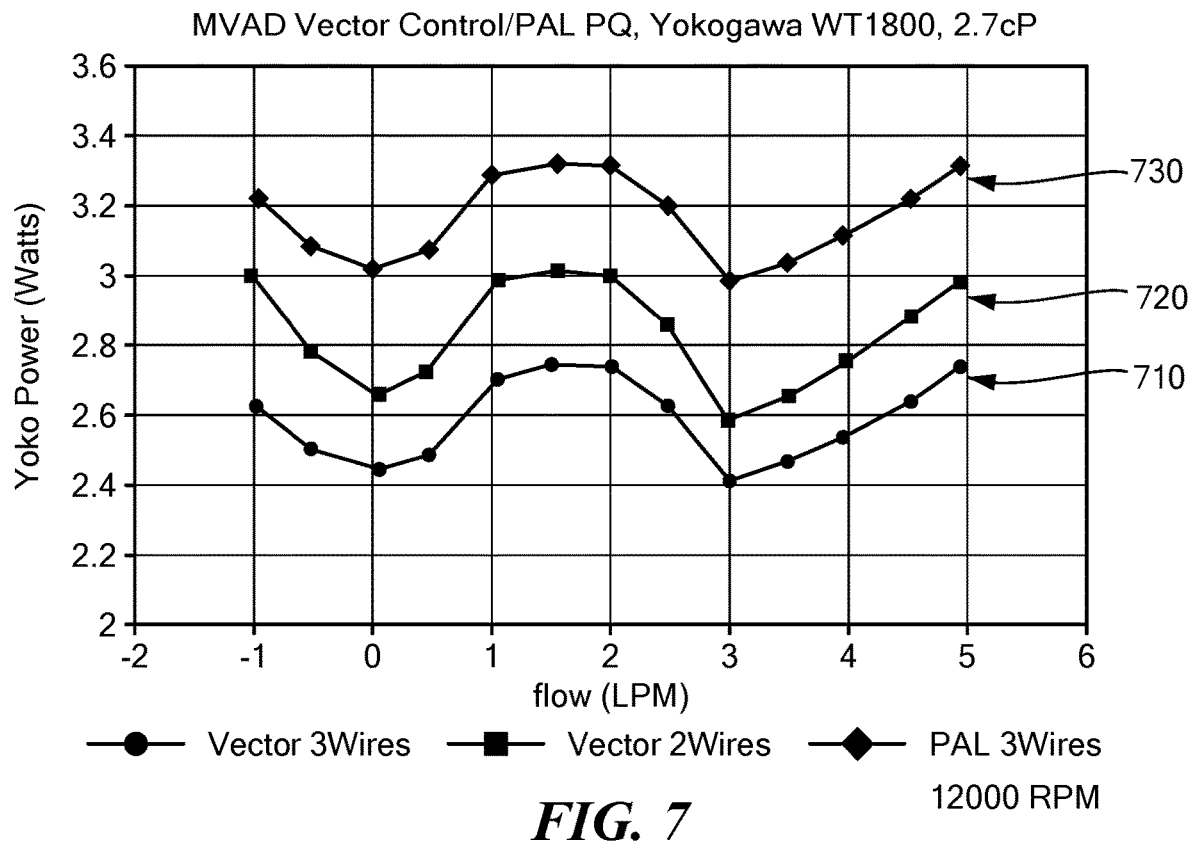
FIG. 7 is a chart illustrating power consumption as a function of fluid flow through an MVAD® pump using field-oriented control as well as using trapezoidal control with the pump operating at 12000 RPM.

FIG. 7 shows power consumption for each of an FOC method using three phases (curve 710), an FOC method using two phases (curve 720) and the PAL PQ method using three phases (curve 730) for the MVAD® operated at 12000 RPM. As can be seen in FIG. 7, both FOC methods result in lower power consumptions for a given flow as compared to that for the PAL method.

Figure 8:
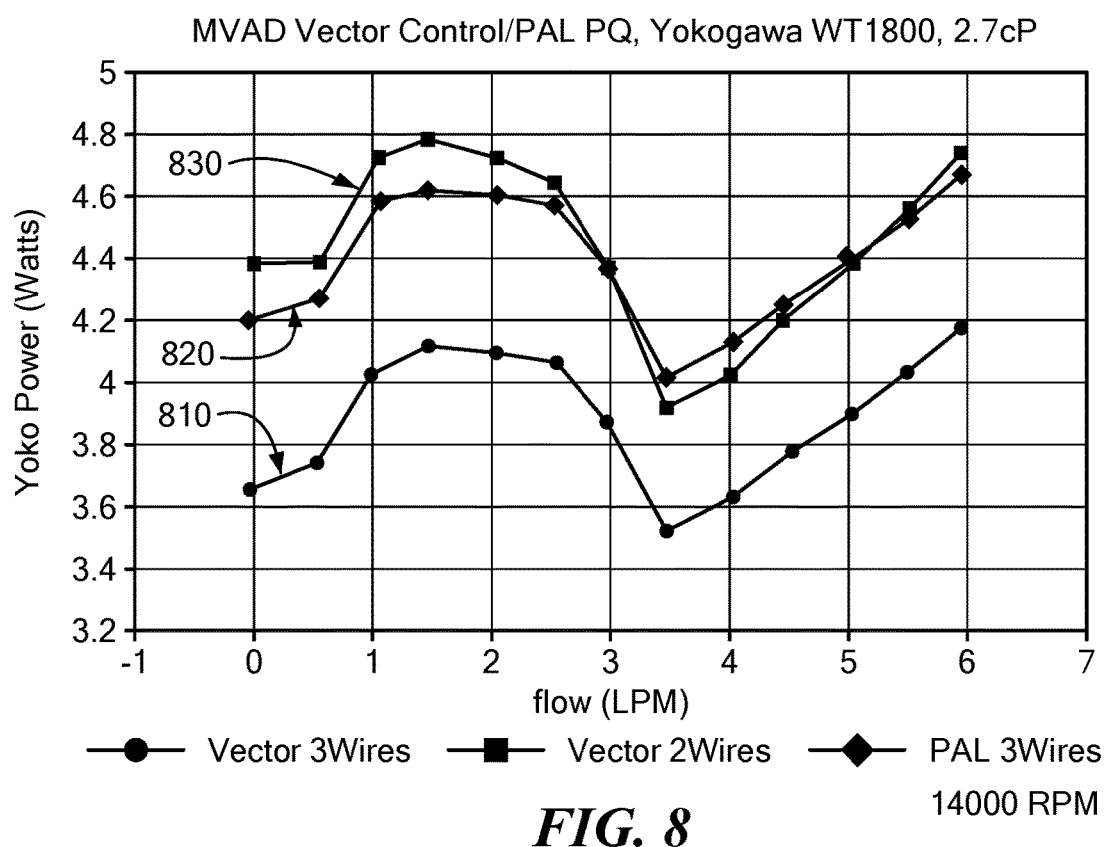
FIG. 8 is a chart illustrating power consumption as a function of fluid flow through an MVAD® pump using field-oriented control as well as using trapezoidal control with the pump operating at 14000 RPM.

Similarly, FIG. 8 shows power consumption for each of an FOC method using three phases (curve 810), an FOC method using two phases (curve 820), and the PAL PQ method using three phases (curve 830) for the MVAD Pump® operated at 14000 RPM. For at least some conditions (e.g., flow between about 3-5 LPM), both FOC methods resulted in lower power consumptions as compared to that for the PAL method.

Figure 9:
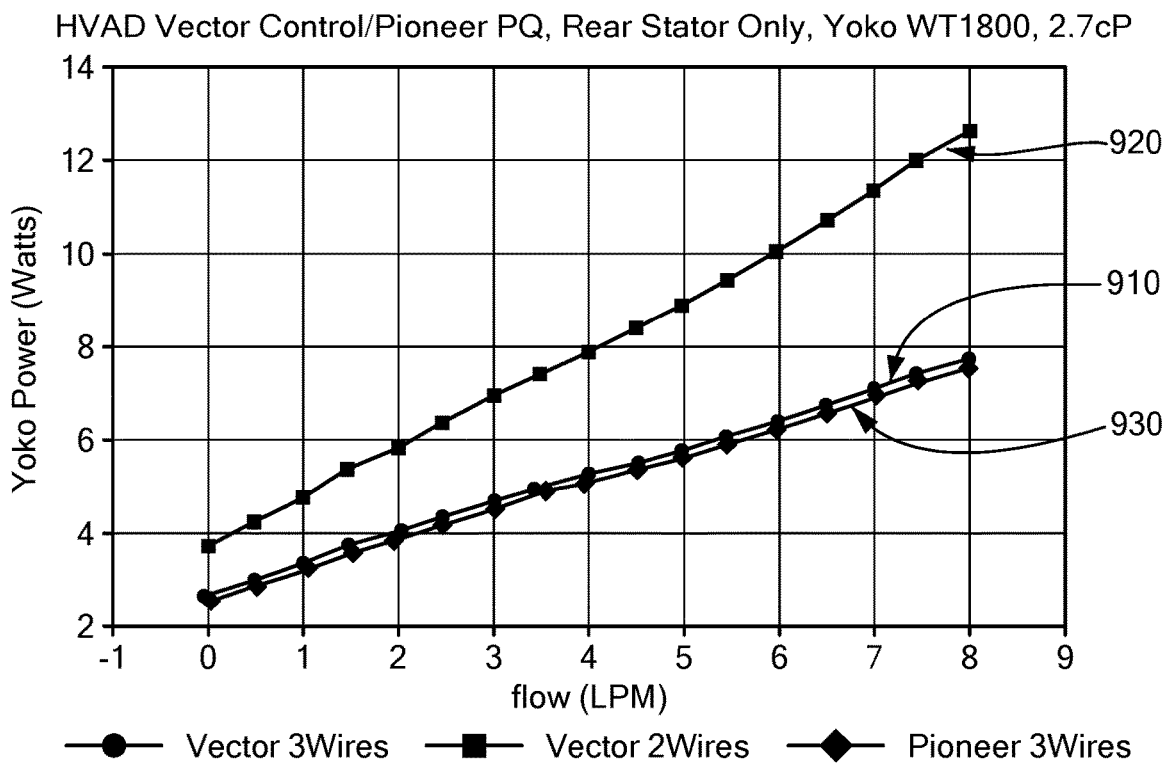
FIG. 9 is a chart illustrating power consumption as a function of fluid flow through a HVAD® pump using field-oriented control as well as using trapezoidal control with the pump operating at 2600 RPM.
Figure 10:
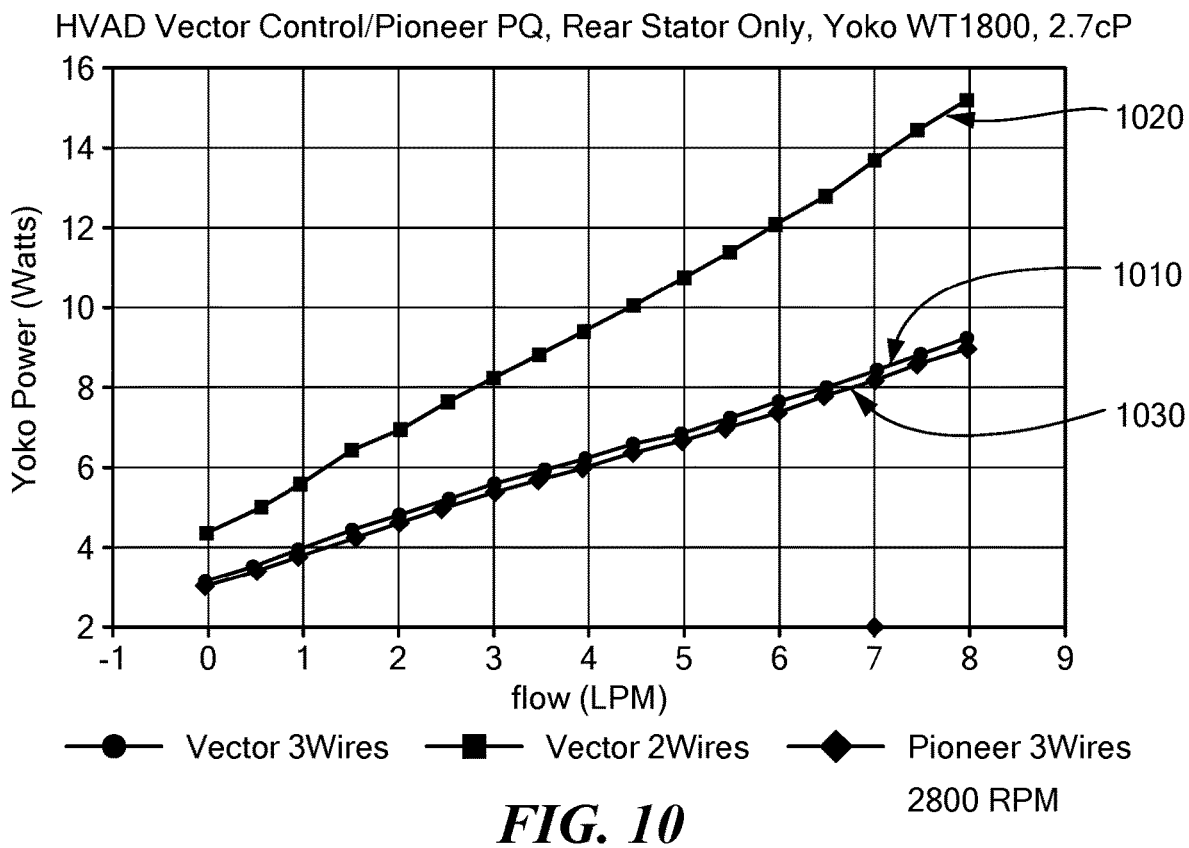
FIG. 10 is a chart illustrating power consumption as a function of fluid flow through a HVAD® pump using field-oriented control as well as using trapezoidal control with the pump operating at 2800 RPM.

FIG. 9 shows power consumption for each of an FOC method using three phases (curve 910), an FOC method using two phases (curve 920) and the Pioneer PQ method using three phases (curve 930) for the HVAD Pump® operated at 2600 RPM, using only the rear stator. FIG. 10 shows power consumption for each of an FOC method using three phases (curve 1010), an FOC method using two phases (curve 1020) and the Pioneer PQ method using three phases (curve 1030) for the HVAD Pump® operated at 2800 RPM, using only the rear stator. While the power consumption for the FOC method using three phases was slightly higher than that for the Pioneer PQ method, the FOC method still provides an advantage in that the HVAD pump may be operated using only two phases with the FOC method, albeit with greater power consumption.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention. It will be appreciated that the various paragraphs and the features set forth therein can be combined in different ways. It will also be appreciated that the features described in connection with individual embodiments may be shared with others of the described embodiments.

What is claimed is:

1. A ventricular assist device, comprising:
a pump configured to pump blood of a patient;
a motor configured to operate the pump;
the pump includes a housing configured for implantation within the body of the patient, the housing having a blood inlet for connection to a ventricle of the patient and a blood outlet for connection to an artery of the patient, wherein the motor is disposed within the housing;
first, second, and third conductors coupled to the motor and configured to supply electric current from a power supply to the motor in first, second, and third phases, respectively; and
a controller configured to operate the motor using a Field Oriented Control (FOC) method, and if one from the group consisting of first, second and third conductors becomes unable to supply electric current to the motor, the controller continues to operate the motor using the FOC method using the phases of the two conductors that are able to supply electric current to the motor.

2. The device of claim 1, wherein the controller is configured to calculate voltage and current vectors, and wherein the controller is configured to commutate the motor based upon the calculated voltage and current vectors.

3. The device of claim 2, further comprising first, second, and third shunts connected to the first, second and third conductors, respectively, wherein the controller is configured to calculate the current vectors using the first, second, and third shunts.

4. The device of claim 1, wherein when one from the group consisting of the first, second, and third conductors is unable to supply current to the motor, the controller is configured to start operation of the motor using the two phases of the conductors that are able to supply current to the motor.

5. The device of claim 1, wherein the controller is configured to output signals representative of vector control variables including a torque and a slip angle of the motor.

6. The device of claim 1 wherein the controller is disposed in a casing remote from the motor, and wherein the controller is electrically connected to the motor.

7. The device of claim 1, wherein the motor is a brushless DC motor, and wherein the power supply connected to the motor is a DC power supply.

8. A method for operating a ventricular assist device, the ventricular device comprising a pump, a motor connected to the pump, a controller connected to the motor, and a power source supplying power to the motor through first, second, and third phase connections, the method comprising:
operating three-phase excitation of the motor through the first, second, and third phase connections to drive the motor and pump using a Field Oriented Control (FOC) method;
determining vector control variables comprising a torque and a slip angle of a rotor of the blood pump, the supply power to the blood pump is controlled by signals representative of the vector control variables; and
if one of the first, second, and third phase connections fails, continuing to drive the motor and pump using the FOC method using the two phase connections that have not failed.

9. The method of claim 8, wherein the controller operates three-phase excitation of the motor based on motor current measurements of the first, second, and third phases provided to the controller from first, second and third shunts, respectively.

10. The method of claim 8, wherein continuing to drive the motor includes starting the motor using the two phase connections that have not failed.

11. A method for operating a blood pump implanted in a patient, the blood pump including a rotor with permanent magnetic poles for rotation around an axis, and a plurality of stator windings in magnetic communication with the magnetic poles of the rotor, comprising:
supplying power to the blood pump using a Field Oriented Control (FOC) method;
determining vector control variables comprising a torque and a slip angle of the rotor, the supply power to the blood pump is controlled by signals representative of the vector control variables; and
if one of the stator windings of the blood pump fails, continuing to supply power to the blood pump over the remaining stator windings using the FOC method.

12. The method of claim 11, wherein the motor is a brushless DC motor, and wherein the method further includes calculating voltage and current vectors and commutating the brushless DC motor based upon calculated voltage and current vectors.

13. The method of claim 12, wherein the current vectors are calculated using a plurality of shunts, each shunt connected to a corresponding stator winding.

14. The method of claim 11, further comprising, if one of the stator windings of the blood pump fails during startup, starting to supply power to the blood pump over the remaining stator windings using the FOC method.

15. A control circuit for operating a blood pump implanted in a patient, the blood pump including a rotor with permanent magnetic poles for rotation around an axis, and a plurality of stator windings in magnetic communication with the magnetic poles of the rotor, the control circuit configured to:
- supply power to the blood pump using a Field Oriented Control (FOC) method; and
- determine vector control variables comprising a torque and a slip angle of the rotor, and the supply of power to the blood pump is controlled by signals representative of the vector control variables; and
- if one of the stator windings of the blood pump fails, continuing to supply power to the blood pump over the remaining stator windings using the FOC method.

16. The control circuit of claim 15, wherein the control circuit is further configured to, during startup of the blood pump, supply power to the blood pump over the remaining stator windings using the FOC method if one of the stator windings of the blood pump fails.

17. The control circuit of claim 15, wherein the control circuit is further configured to calculate voltage and current vectors and to commutate the motor based upon the calculated voltage and current vectors.

\* \* \* \* \*